United States Patent
Prywes

(10) Patent No.: US 10,835,419 B2
(45) Date of Patent: Nov. 17, 2020

(54) METHOD, DEVICE AND SYSTEM FOR TREATMENT OF ELEVATED INTRAOCULAR PRESSURE

(71) Applicant: ASPIP Inc., Melville, NY (US)

(72) Inventor: Arnold Prywes, Bethpage, NY (US)

(73) Assignee: ASPIP INC., Dix Hills, NY (US)

( * ) Notice: Subject to any disclaimer, the term of this patent is extended or adjusted under 35 U.S.C. 154(b) by 335 days.

(21) Appl. No.: 15/998,977

(22) Filed: Aug. 17, 2018

(65) Prior Publication Data

US 2019/0070037 A1    Mar. 7, 2019

Related U.S. Application Data

(60) Provisional application No. 62/546,972, filed on Aug. 17, 2017.

(51) Int. Cl.
| | | |
|---|---|---|
| *A61F 9/007* | (2006.01) | |
| *A61M 27/00* | (2006.01) | |
| *A61F 9/00* | (2006.01) | |

(52) U.S. Cl.
CPC ........ *A61F 9/00781* (2013.01); *A61F 9/0008* (2013.01); *A61F 9/0017* (2013.01); *A61M 27/002* (2013.01); *A61M 2210/0612* (2013.01)

(58) Field of Classification Search
CPC .......................... A61F 9/00781; A61M 27/002
See application file for complete search history.

(56) References Cited

U.S. PATENT DOCUMENTS

| | | | |
|---|---|---|---|
| 5,346,464 A | 9/1994 | Camras | |
| 6,007,511 A | 12/1999 | Prywes | |
| 6,544,249 B1 | 4/2003 | Yu et al. | |
| 6,638,239 B1 | 10/2003 | Bergheim et al. | |
| 6,733,791 B2 | 5/2004 | Mann et al. | |
| 7,192,412 B1 | 3/2007 | Zhou et al. | |
| 7,655,831 B2 | 2/2010 | Prywes | |
| 8,075,511 B2 | 12/2011 | Tu et al. | |
| 8,109,896 B2 | 2/2012 | Nissan et al. | |
| 9,017,276 B2 | 4/2015 | Horvath et al. | |
| 9,782,293 B2 | 10/2017 | Doci | |
| 2002/0188308 A1 | 12/2002 | Tu et al. | |
| 2003/0236483 A1 | 12/2003 | Ren | |
| 2004/0260228 A1 | 12/2004 | Lynch et al. | |
| 2005/0027104 A1 | 2/2005 | Forsgren et al. | |

(Continued)

FOREIGN PATENT DOCUMENTS

GB    2296663 A    7/1996

OTHER PUBLICATIONS

Search Report issued in counterpart PCT International Patent Application No. PCT/US18/00312.

*Primary Examiner* — Leslie R Deak

(74) *Attorney, Agent, or Firm* — Ladas & Parry LLP

(57) ABSTRACT

Apparatus for relieving intraocular pressure in an eye of a subject that includes a plurality of stents, a delivery vehicle for inserting the stents together through a single incision in the cornea of the eye to a position in the anterior chamber adjacent to the trabecular meshwork and an actuator that can be activated from outside of the eye for pushing the stents out of the delivery vehicle and into a plurality of anatomical spaces in the eye from which aqueous from the anterior chamber can be drained. Also, methods for use of the apparatus for controlling the flow of aqueous from the anterior chamber.

12 Claims, 15 Drawing Sheets

(56) References Cited

U.S. PATENT DOCUMENTS

| | | |
|---|---|---|
| 2007/0118147 A1 | 5/2007 | Smedley et al. |
| 2007/0276315 A1 | 11/2007 | Haffner et al. |
| 2007/0293807 A1 | 12/2007 | Lynch et al. |
| 2008/0108933 A1 | 5/2008 | Yu et al. |
| 2008/0221659 A1 | 9/2008 | Hartley et al. |
| 2011/0198281 A1 | 8/2011 | Lynch et al. |
| 2013/0253528 A1* | 9/2013 | Haffner .................. A61F 2/14 606/107 |
| 2018/0036172 A1 | 2/2018 | Haffner et al. |
| 2018/0036173 A1 | 2/2018 | Olson et al. |

* cited by examiner

Triple Implant End View

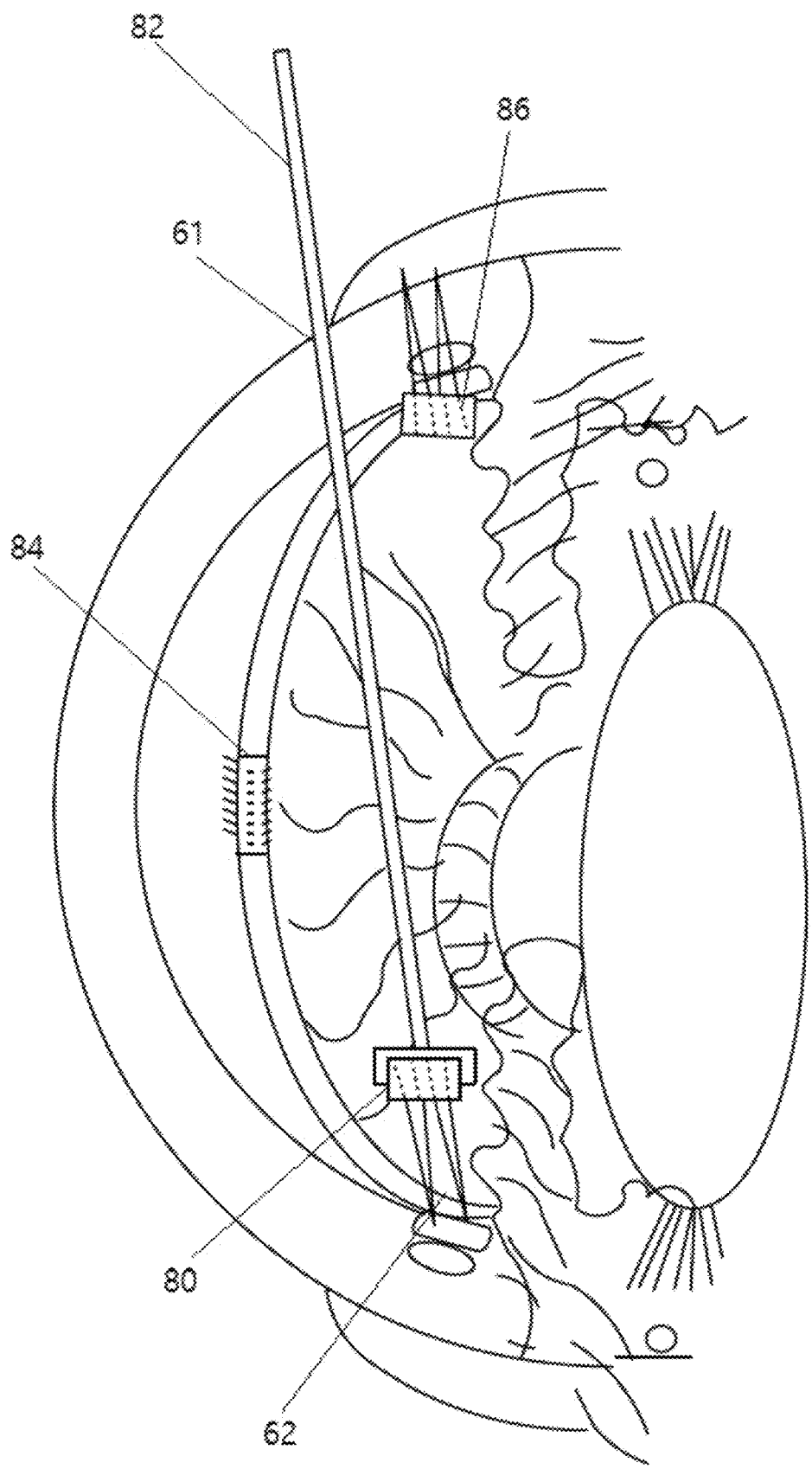

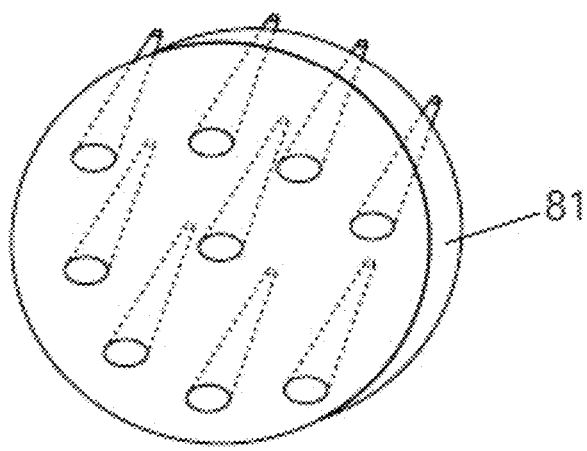
FIG. 8A
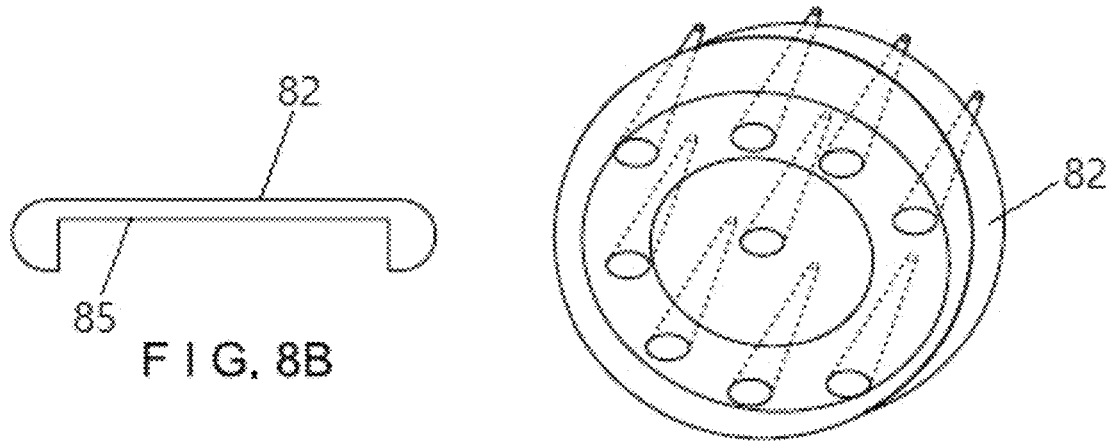
FIG. 8B
FIG. 8C
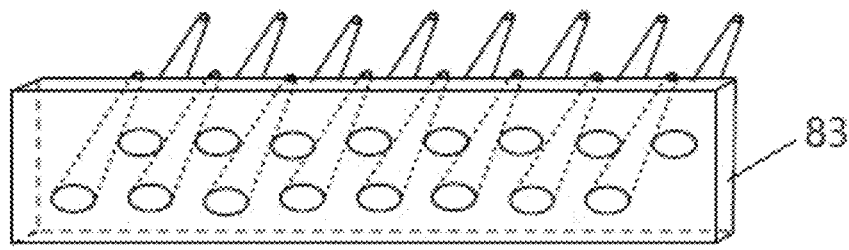
FIG. 8D

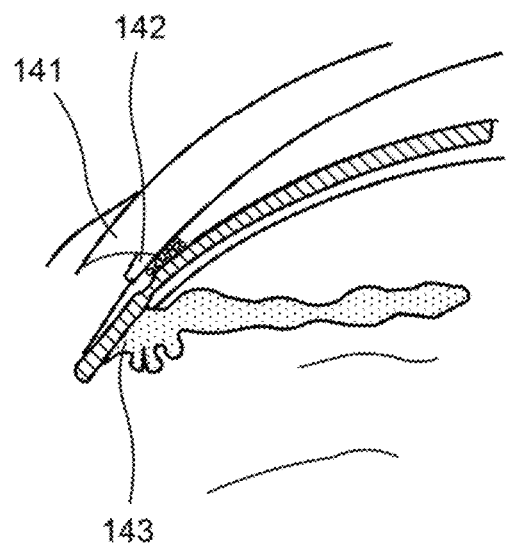
F I G. 16
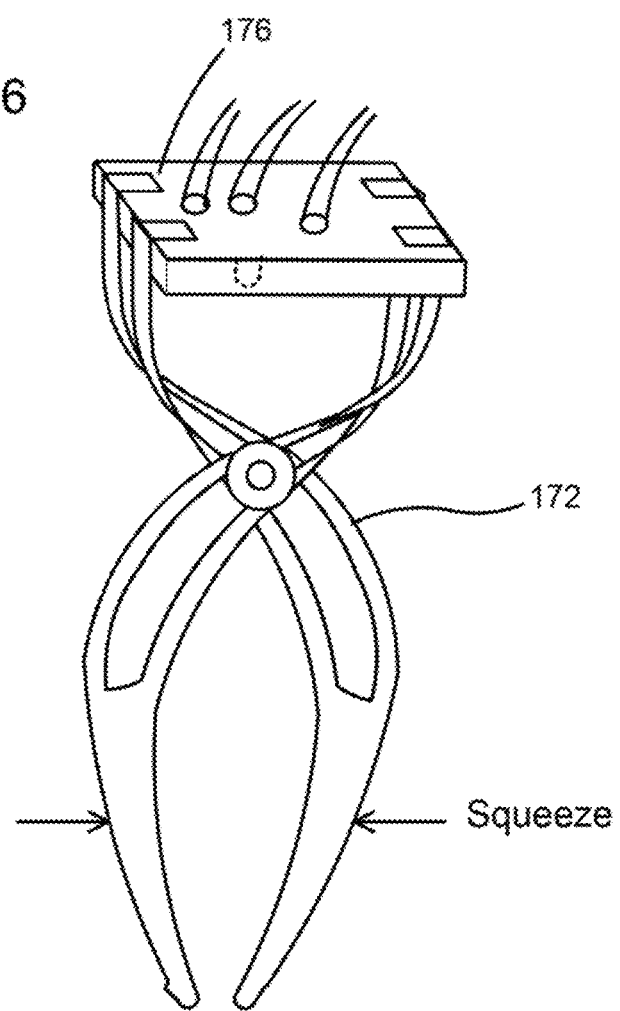
F I G. 17

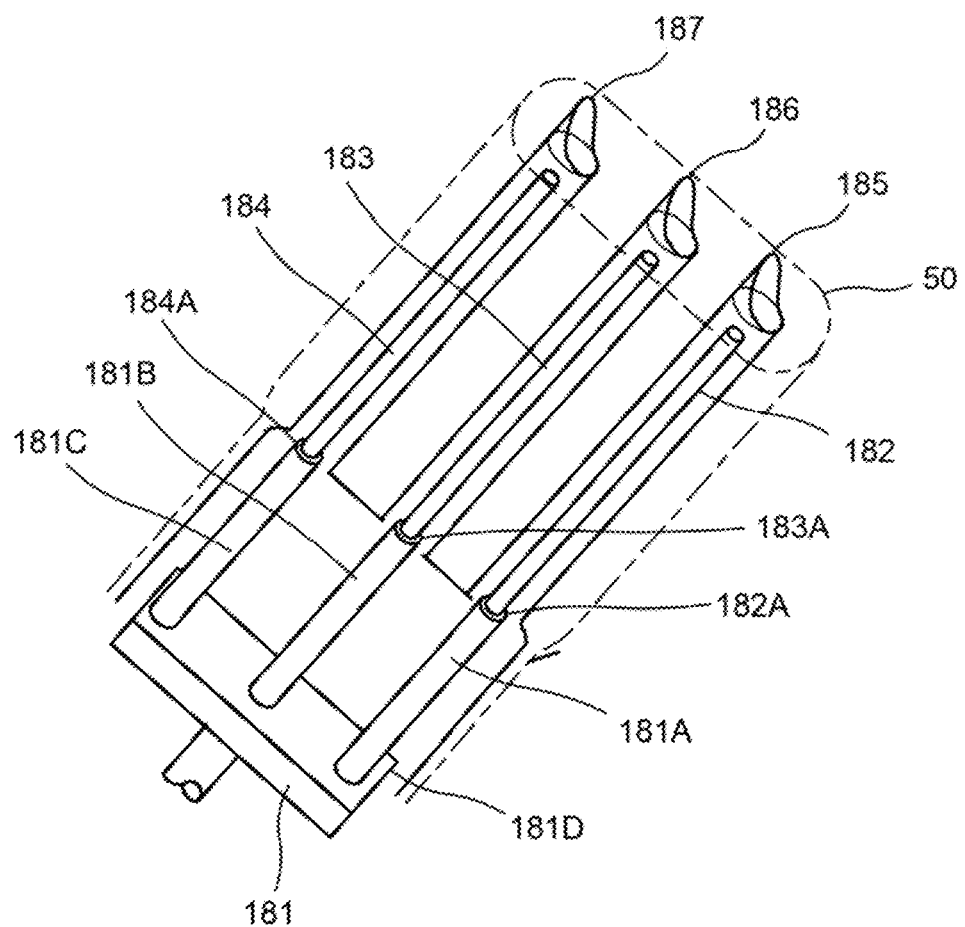
F I G. 18

METHOD, DEVICE AND SYSTEM FOR TREATMENT OF ELEVATED INTRAOCULAR PRESSURE

CROSS-REFERENCE TO RELATED APPLICATION

The present application claims priority wider 35 § 119(e) to U.S. Patent Application No. 62/545,972 filed on Aug. 17, 2017, the disclosure of which in is incorporated by reference herein in its entirety.

BACKGROUND OF THE INVENTION

Glaucoma is a condition whereby the optic nerve is damaged as a consequence of intraocular pressure elevation above the threshold which the optic nerve tolerates. Reducing intraocular pressure is presently the only treatment for slowing the rate of progression of this glaucomatous optic nerve damage. Multiple medical and surgical methods have been employed for lowering intraocular pressure. The medical treatment of glaucoma relies on the use of eye drops which reduce the amount or rate of aqueous humor (the fluid filling the eye) produced within the eye. A further mechanism for lowering intraocular pressure is increasing the outflow of aqueous fluid from the eye which can be accomplished with eye drops or oral medications. The use of topical and systemic (oral) medications have significant side effects which alter the ocular surface, periocular tissues and the interior structures of the eye, as well as affecting the overall health of the patient. Surgical methods also have been described which lower intraocular pressure by producing new outflow channels, or modifying existing outflow channels, or by selectively altering or destroying the fluid producing part of the eye (ciliary processes).

Heretofore the majority of these surgical procedures resulted in significant structural alteration to the eye. Surgical manipulation of the ocular surface in the course of performing surgery for glaucoma is traumatic. The most effective procedures require incising and dissecting the conjunctival, episcleral, and scleral tissues, cautery of the ocular surface, scleral dissection, and removal of iris, trabecular and scleral tissues. The use of sutures to close the surgical wound to close these wounds induce significant inflammation. The resultant complexity and variability in technique make the procedures artisanal. Due to the difficulty in performing the procedures, and their attendant requirement for intensive postoperative care, a minority of ophthalmic surgeons perform these procedures. The reduced safety profile, inconsistent outcomes and lack of efficacy have led to the introduction of newer procedures.

Recently, multiple medical devices have been introduced which seek to reduce the damage to the ocular structures responsible for fluid production and outflow. The goal of these minimally or micro-invasive glaucoma surgeries (MIGS) is increased safety with efficacy comparable to the existing mainstays of glaucoma surgery (trabeculectomy, glaucoma drainage implants, cyclodestruction). These newer procedures increase the surgical armamentarium of eye surgeons and while less effective, have made these procedures surgeries safer than older procedures. For patients with significant glaucoma, MIGS are, at present, not preferred by most glaucoma specialists.

The newer procedures include new methods for implanting glaucoma drainage implants. These implants may be implanted using an ab externo approach (entering through the conjunctiva and inwards through the sclera into the interior of the eye) or an ab interno approach (entering through the cornea, across the anterior chamber, and drainage tissues of the eye, trabecular meshwork, Schlemm's canal, supra-choroidal and subconjunctival space). Traditional ab externo approaches are shown for example in U.S. Pat. No. 8,109,896 to Nissan et al., U.S. Pat. No. 8,075,511 to Tu et al., and U.S. Pat. No. 7,879,001 to Haffner et al., the contents of each of which is incorporated by reference herein in its entirety. Conventional ab interno approaches and devices for use therewith are shown, for example in U.S. Pat. No. 6,007,511 to Prywes, U.S. Pat. No. 6,544,249 to Yu, et al., U.S. Pat. App. Pub. No. US 2008/0108933 A1 to Yu, et al., etc, the contents of each of which is incorporated by reference herein in its entirety.

The traditional ab externo approaches involve surgery in which the conjunctiva, sclera, and sometimes the trabecular meshwork are opened front outside-in. This surgery is not minimally invasive. Methods for placing an implant ab inferno, or ah externo are available. Methods for ah interno implantation require an apparatus that can deliver an implant through the cornea and across the anterior chamber into a suitable position preferably with one, and only one, incision in the cornea.

Existing procedures for glaucoma surgery, including classic trabeculectomy, tube-shunt devices (Ahmed®, Baerveld, Molteno®) and ciliodestructive (Cyclophotocoagulation (CPC), endocylcophotocoanulation (ECP)) and Micro (Minimally) Invasive Glaucoma Surgery (MIGS), are designed to provide treatment of one outflow channel (e.g., CPC) or device (e.g., iStent®, Cypass®, XEN®). Heretofore, ab interno glaucoma surgeries have targeted the outflow channels in the trabecular meshwork, suprachoroidal space, and the subconjunctival space where collector lymphatics drain fluid from the eye. Cyclodestructive procedures have selectively altered or destroyed the fluid producing tissues in the ciliary body.

Ab inferno MIGS procedures presently have heretofore focused on individual outflow pathways. For example, the iStent® (Glaukos) targets the outflow channel of Schlemm's canal by inserting a snorkel-like device which bypasses the trabecular meshwork. This procedure and a device for performing the same is described, for example, in U.S. Pat. No. 6,638,239 to Bergheim, et al., U.S. Pat. No. 6,736,791 to Tu, et al., and U.S. Pat. App. Pub. No. 2005/0271704 to Tu, et al, the contents of each of which are incorporated herein by reference in its entirety. This procedure has been successful for intraocular pressure (IOP) lowering where only mild to moderate reduction is required. It has been used as an adjunct to cataract surgery in most patients with (topical or oral) medications or other surgical procedures being required for further IOP reduction. In the United States, the iStent® is only approved in conjunction with cataract surgery since it is not sufficiently effective in lowering IOP when performed without cataract surgery.

The CyPass® procedure seeks to use the uveoscleral outflow channels of the suprachoroidal space, and with mild to moderate IOP reduction, also only with concomitant cataract surgery due to reduced efficacy. This procedure and a device for use therewith is described, for example, in U.S. Pat. App. Pub. No. 2014/0163448 A1 to Lind, et al., the contents of each of which are incorporated herein by reference in its entirety.

The XEN® gel stent has recently been approved for refractory glaucoma and may be performed without cataract surgery. This procedure and a device for use therewith is described, for example, in U.S. Pat. No. 9,017,276 to Horvath, et al., the contents of each of which are incorporated herein by reference in its entirety. The device bypasses the trabecular meshwork, Schlemm's canal, and sclera draining aqueous fluid into the subconjunctival space. It is non-inferior to trabeculectomy regarding efficacy, while allowing greater safety. The short-term results of all of these MIGS surgeries is promising. However, even with mild to moderate reduction of IOP initially there is frequently a need for further intraocular pressure lowering or intervention while continuing to minimize the complexity of glaucoma surgery.

Heretofore devices which drain into the subconjunctival space have been noted to develop a fibrotic capsule around the ostium (XEN®) gel stent) or drainage plate surface (Molteno®, Baerveldt, Ahmed®). Subconjunctival scarring around the devices requires intervention in a significant number of patients. This reduces their effectiveness in lowering intraocular pressure. The production of inflammatory cytokines in the aqueous is the mechanism demonstrated by Epstein and Freedman, occurring prior to, or soon after, these surgical procedures.

Temporarily obstructing the ostium of the subconjunctival tube in the larger drainage devices has been proven to reduce the fibrosis around the plate of the larger drainage devices. Means for temporarily obstructing the ostium of subconjunctival tubes are described, for example, in the following US patent publications: U.S. Pat. No. 7,655,831 to Prywes, U.S. Pat. No. 5,346,464 to Camras, the contents of each of which are incorporated herein by reference in its entirety.

Unfortunately, a possible consequence of temporarily obstructing, the prior art devices includes marked elevation of IOP, and consequent worsening of glaucoma. Sudden lowering of IOP when the tube occlusion is released may result in significant complications including choroidal effusion, hypotony (severe IOP reduction), bleeding and visual loss. To prevent these complications additional surgical measures have been required. A temporarily functioning trabeculectomy (orphan trabeculectomy), and tube venting punctures (slits), are usually employed to mitigate the problems of IOP elevation and subsequent hypotony, but often are not completely effective until the tube opens. Frequently oral medications (acetazolamide) and multiple topical medications are employed and only partially effective in maintaining safety.

There is thus a need for improved apparatus and methods for treatment of elevated intraocular pressure to prevent the above and other complications from glaucoma surgery.

SUMMARY OF THE INVENTION

The inventor has developed improved devices to deliver and insert implants into the eye of a patient for treatment of elevated intraocular pressure, which devices can be used ab inferno procedures, or in both ab interno and ab externo procedures. These devices have a number of advantages over prior art devices, including that they are insertable through a single incision in the cornea and, in one embodiment, can be used to attack multiple loci of the same outflow pathway (e.g., subconjunctival space. Schlemm's Canal or suprachoroidal space) and, in another embodiment, can be used to attack single or multiple loci of multiple outflow pathways (e.g., Schlemm's Canal, suprachoroidal, and subconjunctival space). These devices can be used to make MIGS more successful while reducing complications. For example, with multiple channels for outflow of aqueous from the anterior chamber, or with multiple outflow pathways of aqueous from the anterior chamber, it is possible to obstruct a single channel or pathway temporarily, thereby reducing inflammatory cytokine outflow and subsequent fibrosis around an outflow port with reduced risk of marked elevation or severe reduction of IOP in the anterior chamber.

In accordance with a first embodiment of the invention, there is provided an apparatus for relieving intraocular pressure in an eye of a subject comprising:

(a) a plurality of stents, including at least (i) a first stent sized and configured for being implanted in the eye through a hole in a first membrane separating a high pressure chamber of the eye from a first anatomical space of lower pressure than the high pressure chamber in a first disposition with an inlet end of the first stent in the high pressure chamber and an outlet end of the first stent in the first anatomical space to permit drainage of fluid from the high pressure chamber to the first anatomical space and with a portion of the first stent engaging with the first membrane to stabilize and retain the first stent in the first disposition, and (ii) a second stent sized and configured for being implanted in the eye through a hole in a second membrane separating the high pressure chamber of the eye from a second anatomical space of lower pressure than the high pressure chamber in a second disposition with an inlet end of the second stent in the high pressure chamber and an outlet end of the second stent in the second anatomical space to permit drainage of fluid from the high pressure chamber to the second anatomical space and with a portion of the second stent engaging with the second membrane to stabilize, and retain the second stent in the second disposition; wherein the high pressure chamber is the anterior chamber of the eye, and wherein each of the first and second anatomical spaces is selected from the group consisting of a subconjunctival space, Schlemm's canal and a suprachoroidal space, wherein the first anatomical space and the second anatomical space can be different areas of the same anatomical space;

(b) delivery means for releasably carrying at least the first stent and the second stent together through a single incision in the cornea of the eye to a first position in the anterior chamber of the eye that is adjacent the trabecular meshwork and for holding the first and second stents at said position in an anterior to posterior configuration until the first and second stents are released from the delivery means, the delivery means comprising means for forming respective holes in the first and second membranes through which the first and second stents are insertable or each of the first and second stents comprising a sharpened end for forming respective holes in the first and second membranes through which the first and second stents are respectively insertable; the first and second stents being disposed in the delivery means and being respectively sized and configured such that, with the delivery means in the first position and with application of a force to each of the first and second stents, each of the first and second stents is releasable from the delivery means and implantable into the eye through the respective holes formed in the first and second membranes and into the first and second dispositions respectively; and (c) actuating means for applying a force to each of the first and second stents to cause the first and second stents to be released from the delivery means and implanted into the eye with the first and second stents in the first and second dispositions respectively.

In a preferred aspect of this embodiment, the apparatus comprises mean s for temporarily occluding drainage of fluid passing through the first stent from the anterior chamber into the subconjunctival space with the first stent implanted into the eye in the first disposition without occluding drainage of fluid through the second stent.

In another preferred aspect of the first embodiment, the delivery means comprises a cannula having an anterior surface and a posterior surface and at least first and second channels for retaining the first and second scents respectively with a friction fit, wherein the cannula comprises means for differentiating the anterior and posterior surfaces, and wherein the first stent and the second stent are disposed within the cannula in an anterior to posterior orientation.

In a further preferred aspect of this first embodiment, the first stent is disposed in the delivery means and is sized and configured for implantation into the eye with the inflow end of the first stent in the anterior chamber and the outflow end of the first stent in the subconjunctival space and the second stent is disposed in the delivery means and is sized and configured for implantation into the eye with the inflow end of the second stent in the anterior chamber and the outflow end of the second stent in Schlemm's canal.

In another preferred aspect of this first embodiment, the first stent is disposed in the delivery means and is sized and configured for implantation into the eye with the inflow end of the first stent in the anterior chamber and the outflow end of the first stent in the subconjunctival space and wherein the second stent is disposed in the delivery means and is sized and configured for implantation into the eye with the inflow end of the second stent in the anterior chamber and the outflow end of the second stent in the suprachoroidal space.

In yet another preferred aspect of the first embodiment, the first stent is disposed in the delivery means and is sized and configured for implantation into the eye with the inflow end of the first stent in the anterior chamber and the outflow end of the first stent in Schlemm's canal and wherein the second stent is disposed in the delivery means and is sized and configured for implantation into the eye with the inflow end of the second stent in the anterior chamber and the outflow end of the second stent in the suprachoroidal space.

In a still further preferred aspect of the first embodiment, the plurality of stents further comprises a third stent, the third stent being sized and configured for being implanted in the eye through a hole in a third membrane separating the anterior chamber of the eye from a third anatomical space of lower pressure than the anterior chamber in a third disposition with an inlet end of the third stent in the anterior chamber and an outlet end of the third stent in the third anatomical space to permit drainage of fluid from the anterior chamber to the third anatomical space and with a portion of the third stent engaging with a third membrane to stabilize and retain the third stent in the third disposition, the hole forming means comprising means for forming a hole in the third membrane through which the third stent is insertable or the third stent comprising a sharpened end for forming a hole in the third membrane through which the third stent is insertable; the first, second and third stents being disposed in the delivery means and being sized and configured such that, when the delivery means is in the first position adjacent to the trabecular meshwork and an actuation force is applied to each of the first, second and third stents, the first, second and third stents are implantable into the eye in the first, second and third dispositions respectively with the inflow end of the first stent in the anterior chamber and the outflow end of the first stent in the subconjunctival space, with the inflow end of the second stent in the anterior chamber and the outflow end of the second stent in Schlemm's canal and with an inflow end of the third stent in the anterior chamber and an outflow end of the third stent in the suprachoroidal space.

In accordance with yet another preferred aspect of this embodiment, the actuating means comprises a first mechanism comprising a first end with a first member that is slidable along a first surface of the cannula when pushed by a thumb or finger of a user, the first mechanism having a second end with means for simultaneously pushing the first, second and third stents out of their respective channels and implanting them into the eye in the first, second and third dispositions respectively when the first slidable member is slid along the first surface toward the first, second and third stents.

In accordance with a second embodiment of the invention, there is provided an apparatus for relieving intraocular pressure in an eye of a subject comprising a multi-sided body made of biocompatible material suitable for implanting into the eye, the body comprising opposing first and second sides with the first side having at least one opening and the second side comprising an array of tubular projections projecting therefrom, the at least one opening on the first side of the body being in fluid communication with the array of projections projecting from the second side of the body, the body and the plurality of projections being sized and configured such that the apparatus is insertable into the anterior chamber of the eye through a single incision and is implantable into a position in the anterior chamber of the eye with the second side of the body contacting the chamber angle of the eye and with each projection of the array of projections projecting into the chamber angle and into an anatomical space selected from the group consisting of a subconjunctival space, Schlemm's canal, a suprachoroidal space and a combination thereof so as to stabilize and retain the implant in the position in the anterior chamber and to permit drainage of fluid from the anterior chamber into the selected anatomical space or spaces.

In a preferred aspect of this second embodiment, the apparatus comprises means for delivering the body into the eye through a single incision in the anterior chamber and for implanting the body into the position in the anterior chamber with the second side of the body contacting the trabecular meshwork. In one aspect, the delivery means comprises forceps with a clamping mechanism for holding the body until the array of projections are implanted into the eye and a release mechanism for remote release of the clamping mechanism such that the forceps can be delivered to the implantation site through an incision in the cornea and can be released by an operator (surgeon) outside of the eye.

In accordance with a further preferred aspect of this embodiment, each of the plurality of projections has a sharpened tip for penetrating in and through the trabecular meshwork. In another preferred embodiment, each of the projections in the array of projections has a conical shape and projects from the second side of the body at an acute or obtuse angle.

In accordance with a still further preferred aspect of the second embodiment, at least a subset of the array of projections projects into the subconjunctival space and the apparatus comprises means for temporarily occluding drainage of fluid passing through at least one projection in the subset of projections without occluding drainage of fluid passing through one or more other projections in the array.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure.

FIG. 6 illustrates an exemplary shunt tack embodiment of the invention showing delivery and implantation of the tack shunt into the anterior chamber ab interno.

FIGS. 8A-D are perspective views of exemplary shunt tack embodiments of the present invention.

FIG. 16 is a cross sectional view showing respective subconjunctival, suprachoroidal, and trabecular stents in situ in the eye.

FIG. 17 is a perspective view of a forceps delivery vehicle for insertion of a deck with an array of shunts into the eye.

FIG. 18 is a perspective view of a delivery vehicle for carrying three (3) stents inside channels, a guide wire and an actuator for causing the stents to be inserted into a single outflow pathway in an eye.

DETAILED DESCRIPTION OF THE PREFERRED EMBODIMENTS

Figure 1:
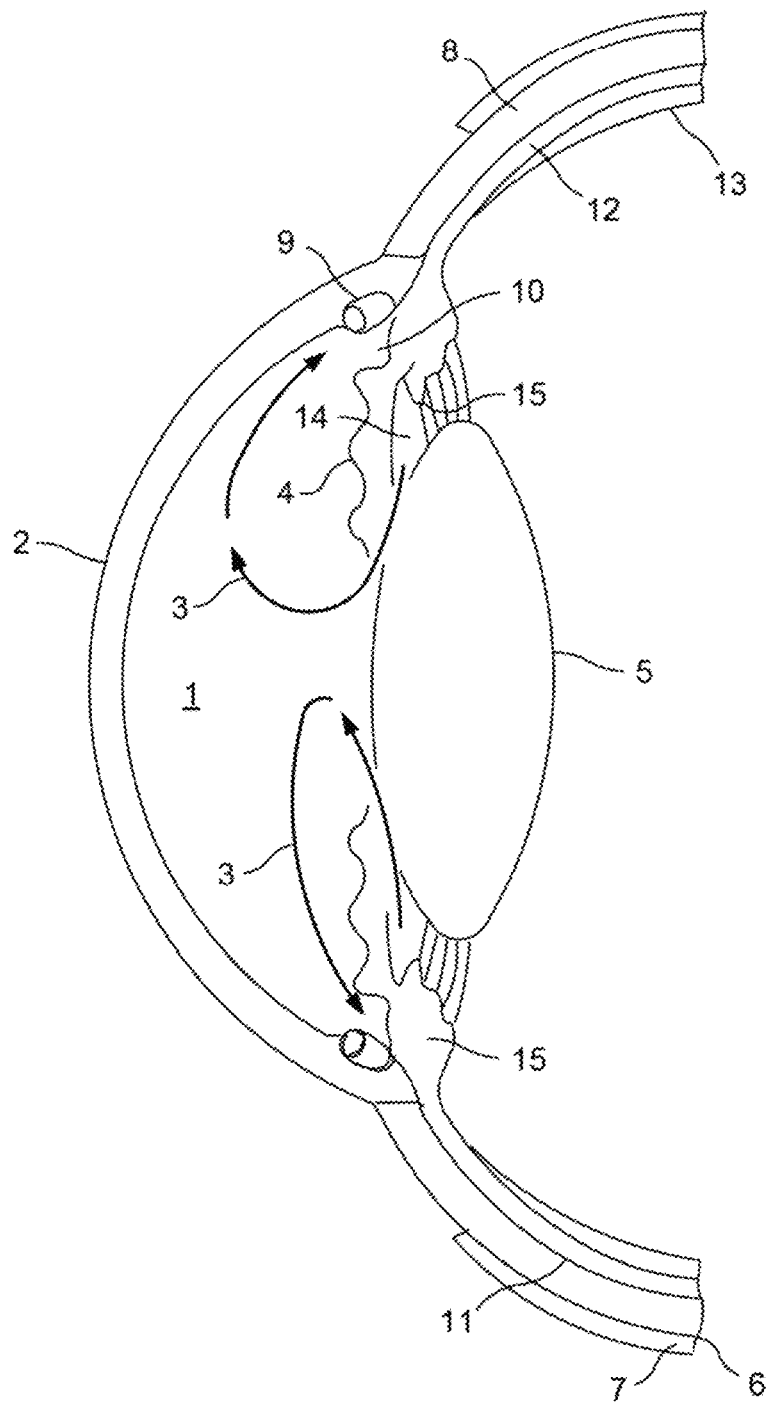
FIG. 1 illustrates a cross section of the anatomy of the anterior chamber and preferred outflow channels.

Referring to FIG. 1, therein is shown a simplified and diagrammatic illustration of the eye structure in the minimum detail to illustrate the invention in a clear fashion. The anterior aspect of the anterior chamber 1 of the eye is the cornea 2 whereas the posterior aspect is the iris 4 beneath which is the lens 5. The anterior chamber 1 is filled with aqueous humor 3. The aqueous humor 3 drains into the subconjunctival space 6 through the trabecular meshwork 10 of the sclera 8. The aqueous humor is drained from the subconjunctival space 6 through a venous drainage system (not shown). The subconjunctival space 6 is formed between the conjunctiva 7 and the sclera 8. Schlemm's canal 9 is located peripheral to the trabecular meshwork 10. The suprachoroidal space 11 is a space between the sclera 8 and the choroid 12, which is known to, provide a pathway for uveoscleral outflow. Below the choroid 12 is the retina 13.

In conditions of glaucoma, the pressure of the aqueous humor in the eye (anterior chamber) increases and this resultant increase of pressure can cause damage to the vascular system at the back of the eye and especially to the optic nerve. The treatment of primary glaucoma, and other diseases which lead to elevated pressure in the anterior chamber (secondary glaucoma), involves relieving pressure to a normal level.

Figure 2:
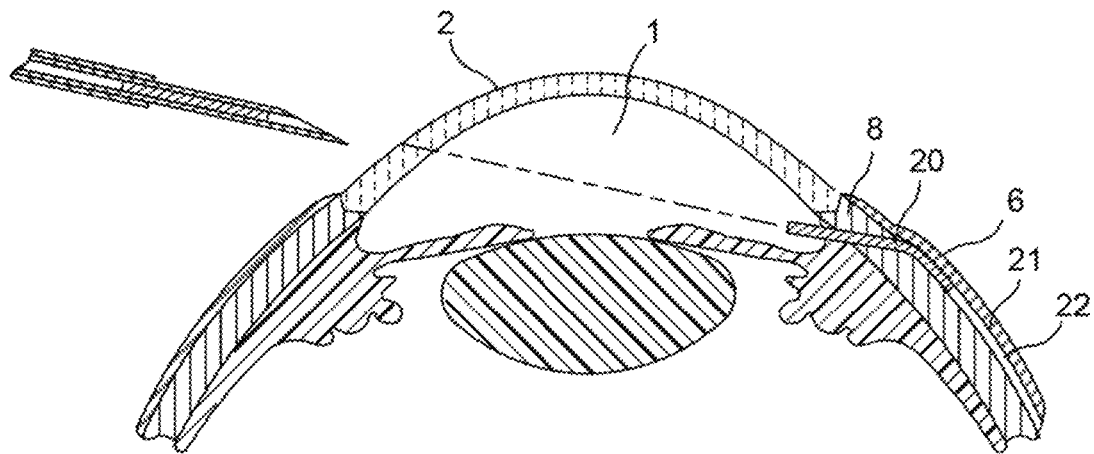
FIGS. 2-4 illustrate exemplary stents or shunt valves that have been used in the prior art to drain aqueous from the anterior chamber to different anatomical spaces to relieve the intraocular pressure in the anterior chamber.
Figure 3:
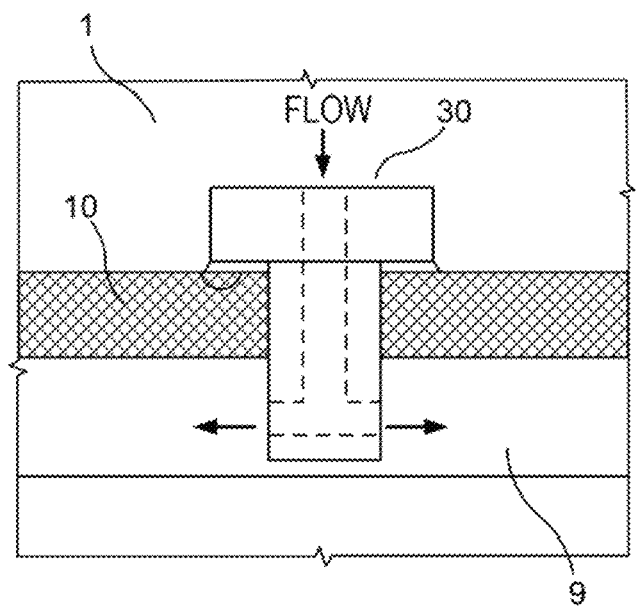
Figure 4:
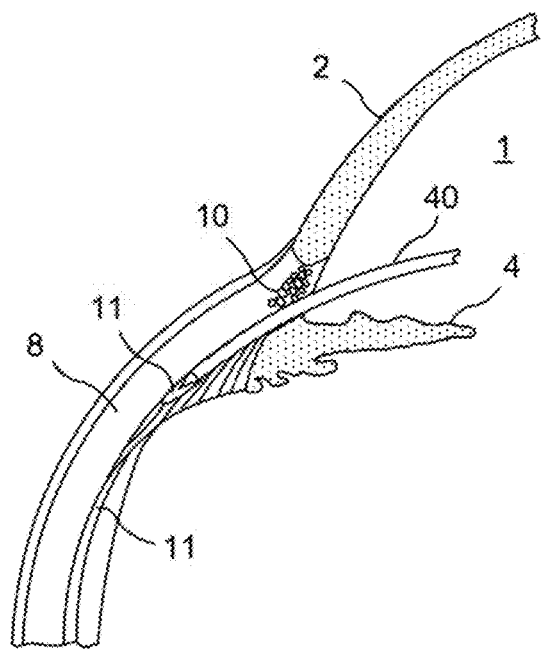

FIGS. 2, 3 and 4 illustrate examples of stents or shunt valves 20, 30 and 40 that have been used in the prior art to relieve the intraocular pressure in the anterior chamber by providing a flow path from the anterior chamber to the subconjunctival space (FIG. 2), Schlemm's canal (FIG. 3) and the suprachoroidal space (FIG. 4) respectively. FIG. 2 shows a shunt valve 20 of the prior art comprising a tubular body having an outer surface engaging the sclera with the valve implanted through the sclera with an inflow end of the valve in the anterior chamber and an outflow end of the valve in the subconjunctival space. FIG. 3 shows a shunt valve 30 of the prior art comprising a tubular body having an outer surface engaging the trabecular meshwork with the valve implanted through the trabecular mesh and into Schlemm's canal. FIG. 4 shows a shunt valve 40 of the prior art comprising a tubular body passing through the trabecular meshwork with the valve implanted in the suprachoroidal space. The respective stents may be sized and configured to engage the respective wall or membrane separating the anterior chamber from the respective anatomical spaces in an installed position. Each of the valves 20, 30 and 40 has an axial bore extending completely there through to establish communication between the anterior chamber and a respective one of the anatomical spaces with the valves in the installed position.

Unlike the prior art devices, each of which is implantable ab interno for providing an outflow pathway to a single anatomical space only, the devices according to one embodiment of the invention are implantable ab inferno and comprise a multiplicity of fluid outflow orifice means (ports) directed at a plurality of fluid (aqueous) outflow pathways within the eye. In a preferred embodiment, the device comprises three outflow means for tri-flow of aqueous from the anterior chamber to Schlemm's canal, suprachoroidal bypass, and subconjunctival space respectively. In another embodiment, two outflow channels are provided for dual- or bi-flow of aqueous to two anatomical spaces selected from the group consisting of (a) the subconjunctival space and Schlemm's canal, (b) the subconjunctival space and the suprachoroidal space and (c) the suprachoroidal space and Schlemm's canal.

Figure 5:
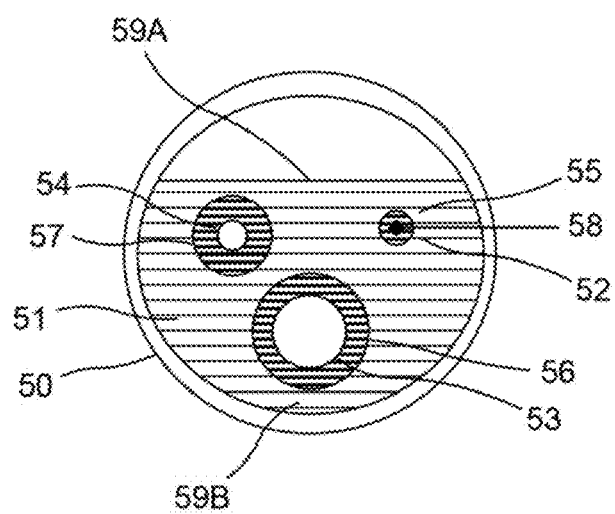
FIG. 5 is an end view of an exemplary delivery vehicle comprising a cannula for delivery of three (3) stents according to one embodiment of the present invention.
Figure 7A:
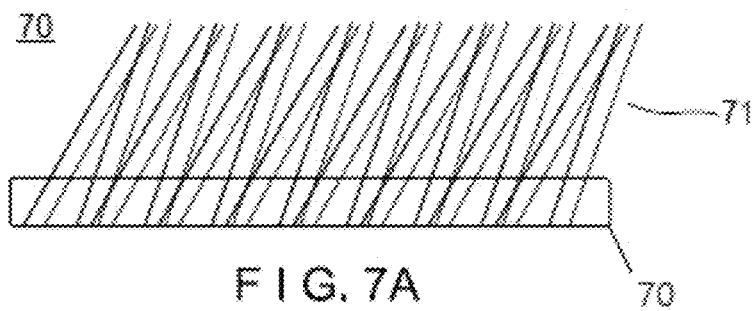
FIGS. 7A-G are perspective and side views of an exemplary shunt tack device according to one embodiment of the present invention.
Figure 7B:
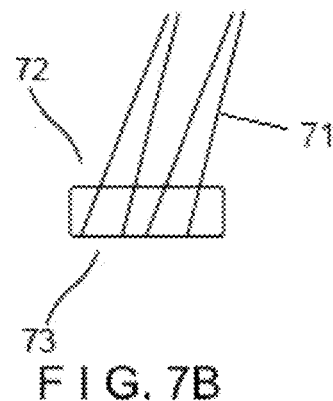
Figure 7C:
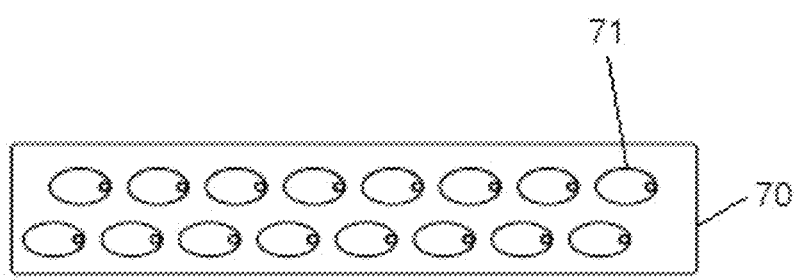
Figure 7D:
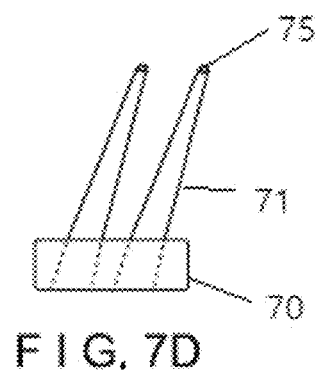
Figure 7E:
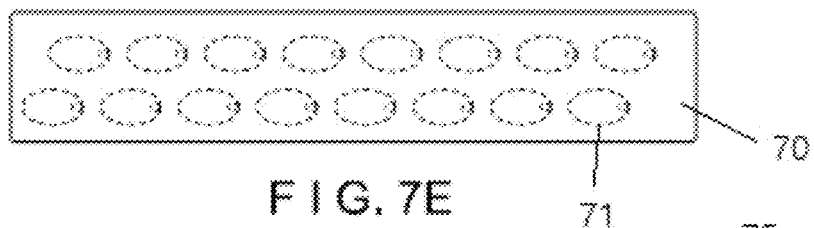
Figure 7F:
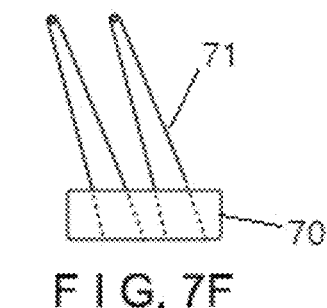
Figure 7G:
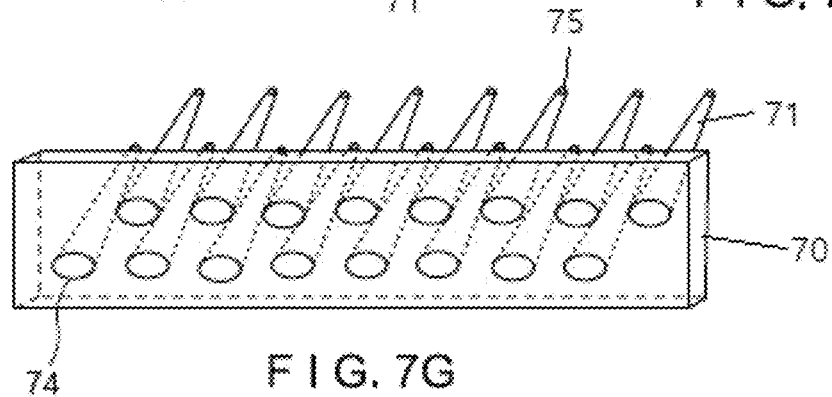

Referring to FIG. 5, therein is seen a cannula 50, a preferred delivery vehicle of the invention, in which a plurality of stents 55, 56 and 57 can be together delivered to a position within the anterior chamber of an eye adjacent the trabecular meshwork for implantation of the stents into the subconjunctival space, Schlemm's canal and the suprachoroidal space respectively. The cannula 50 contains an implant base 51 comprising tubes or channels with lumens 52, 53, and 54 for carrying a subconjunctival stent 55, a suprachoroidal stent 56 and a canal stent 57 that have been inserted into the respective lumens with a frictional fit. The stents for insertion in the lumens of the respective channels can be those depicted in FIGS. 2, 3, and 4 or any other stent(s) that can perform the desired function of draining aqueous from the anterior chamber to the respective anatomical spaces, including stents that have been used in the prior art for insertion into the eye ab interno for draining to each of the anatomical, spaces individually. One or more of the stents may be loaded onto a guidewire 58 before insertion into the eye, and the guidewire may be used to locate the stent to the targeted space. The guidewire 58 has a lumen of a size that is, by way of example, approximately 150 micron in diameter. The stent may be released from the guidewire when the guidewire has placed the stent at a desired anatomical space in the eye. After the stent is released from the delivery device, the guidewire can be retracted. FIG. 5 shows the relative diameters of the identified stents in a preferred embodiment of the invention, but the diameter of each stent 55, 56, and 57 could be made larger or smaller.

The stents 55, 56 and 57 contain bores extending there through for draining fluid from the anterior chamber to the respective anatomical spaces. The outer surfaces of the respective stents may preferably be provided with slots or other means for enhancing frictional engagement with respective membranes through which they are inserted. The thickness of the slots can be such as to enable the stents to engage the respective membranes through which they are inserted to maintain the stents in a secure position against fore and aft movement so that the open ends of the tubular body will respectively communicate with the anterior chamber and the respective anatomical spaces for allowing flow of aqueous fluid from the anterior chamber to the respective anatomical spaces.

The geometry of the base can be such as to provide an indication of the respective orientation of the stents in the cannula 50. For example, in FIG. 5 the top 59A of the implant base is flat whereas the bottom 59B of the implant base is rounded.

The stents or shunt valves can be made of a conventional plastic material such as polymethyl methacrylate, silicone or the like. The valves can also be made of a hydrophilic substance which will swell upon contact with the aqueous humor. Known hydrogels serve this function. Surgical steel, titanium and other non-reactive metals or alloys which are biocompatible may be used for this purpose. The valve can also be made of a material which slowly dissolves in the aqueous humor, such as collagens, and they can contain medications such as anti-inflammatory, anti-thrombotic, anti-scarring, anti-cross-linking and immuno suppressive agents.

The composition of the material of the valve shunts or stents and their dimensions can be selected to provide a certain amount of flexibility for the valves allowing them to deform elastically, for example, to an arcuate shape, to facilitate installation into an anatomical space. The valves can return to their initial position after such elastic deformation. All or a portion of a valve shunt may be naturally curved to conform to the curvature of the globe of the eye or otherwise to facilitate insertion of the valve shunt, particularly when the valve shunt is targeted for delivery to the subconjunctival and suprachoroidal space.

Referring to FIG. 5, the respective stents are disposed in the cannula to facilitate their implantation in the eye in respective dispositions that enable drainage of aqueous from the anterior chamber to the respective anatomical spaces. In this connection, the subconjunctival stent 55 and the canal stent 57 are disposed in the cannula 50 closer to the anterior surface of the cannula than the suprachoroidal stent 56. The cannula is preferably circular or ovoid in shape with an outer diameter of 1000 to 1500 µm. The subconjunctival stent preferably has an outer diameter of 150 to 400 µm with a lumen of its tubular body between 10-150 µm. The trabecular meshwork/Schlemm's canal stent preferably has an outer diameter of 200 to 400 µm and a lumen of its tubular body of between 70-150 µm. The suprachoroidal stent preferably has an outer diameter of 300 to 500 mm and a thickness a lumen of its tubular body between 100-200 µm.

Figure 13:
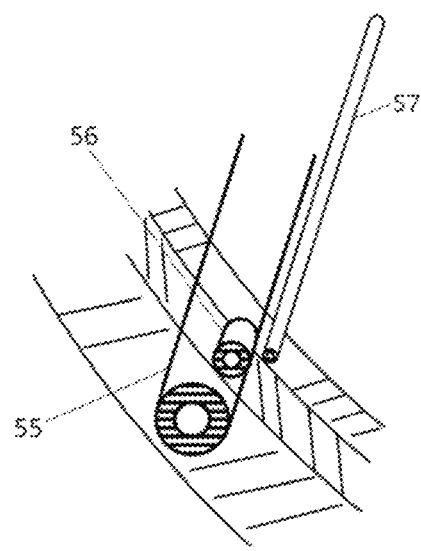
FIG. 13 illustrates three (3) stents in situ after being implanted in separate anatomical spaces in the eye according to one embodiment of the present invention.
Figure 14:
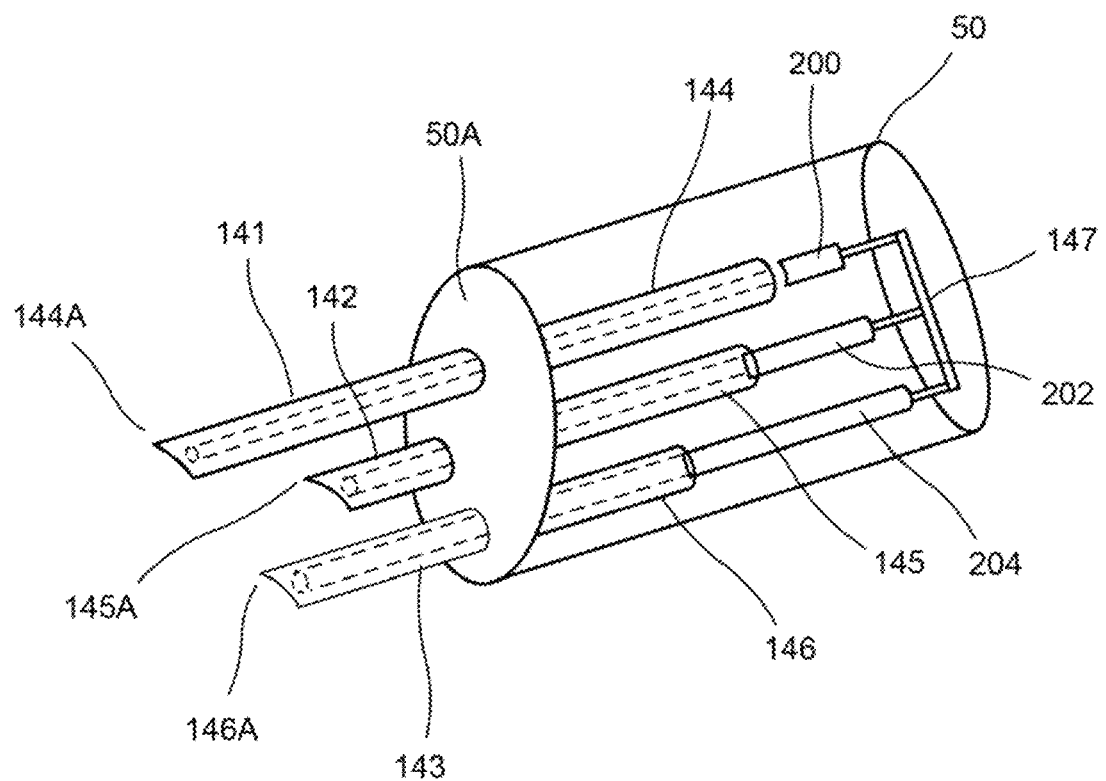
FIG. 14 is a perspective view of a delivery vehicle releasably carrying three (3) stents in respective tubular channels and an actuator for pushing the stents out of the channels according to one embodiment of the present invention.

FIG. 14 shows a perspective view, of a cannula similar to that shown in FIG. 5, FIG. 14 depicts a cannula 50 comprising tubular channels 144, 145, and 146 with sharpened edges at tips 144A, 145A, and 146A of each channel carrying subconjunctival stent 141, trabecular meshwork/Schlemm's canal stent 142 and suprachoroidal stent 143 releasably contained in the channels with a friction fit. As shown in FIG. 14, channels 144, 145, and 146 can be provided with sharpened ends 144A, 145A, and 146A for forming holes in respective membranes of the eye through which the stents can pass when implanted. The channels 144, 145 and 146 are of respective lengths sufficient to deliver the respective stents contained therein to the respective anatomical spaces for which they are targeted. Plunger 147 is provided with prongs 200, 202 and 204 to push the respective stents out of cannula 50, through the holes formed by the sharpened ends of the channels and into targeted spaces in the eye. The respective lengths and dispositions of the stents and prongs are selected to insure implantation of the stents with their respective outflow ends in the respective anatomical spaces for which they are targeted. Preferably, the subconjunctival stent 141 will have a length of between 6 to 9 mm; the suprachoroidal stent 143 will have a length of between 4 to 7 mm; and the canal stent 142 will have a length of between 3 to 8 mm. The stents 55, 56, and 57 can be delivered simultaneously with plunger 147. FIG. 13 shows the stents 55, 56 and 57 delivered into respective anatomical spaces in the eye.

Figure 21:
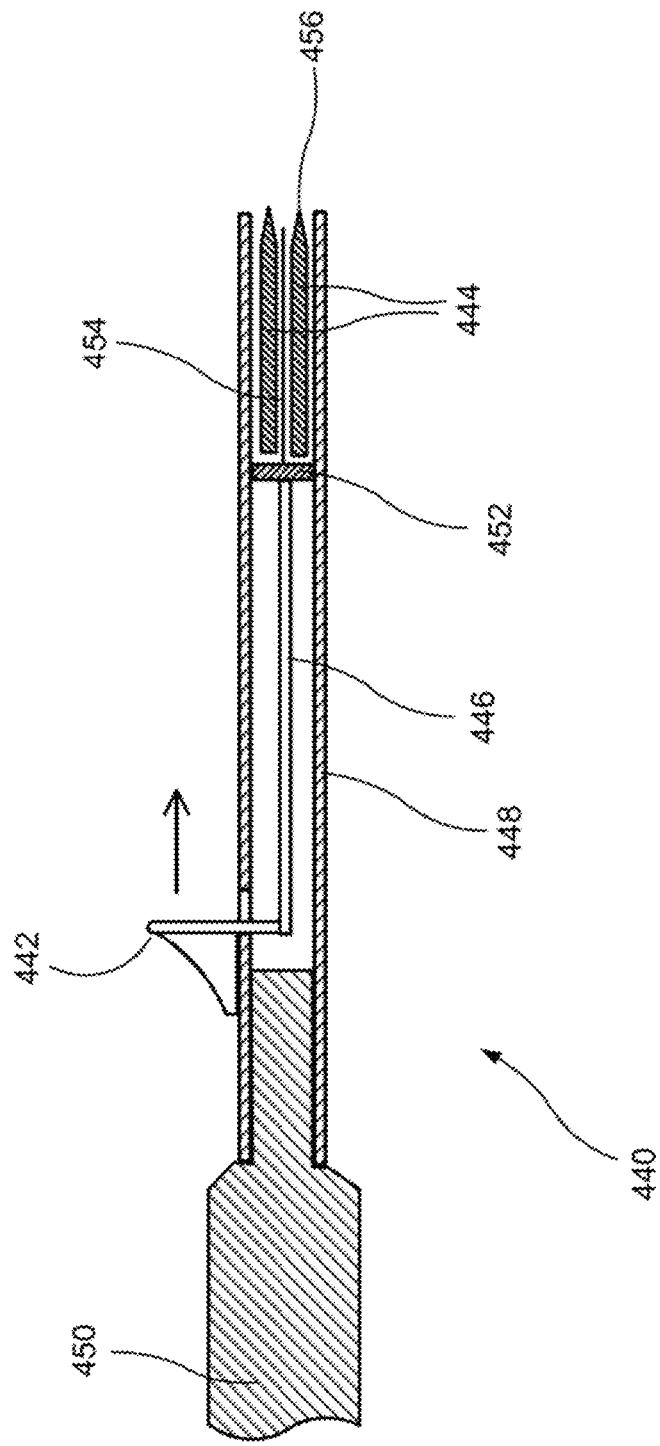
FIG. 21 illustrates a finger actuator for ab interno delivery of one or more stents into an eye of a patient.

FIG. 14 shows one plunger 147 for use in simultaneously implanting the three stents 55, 56, and 57. It may be appreciated, however, that in an alternative embodiment one plunger can be used to deliver two of the stents simultaneously and a separate plunger can be used to deliver the third stent. It is also possible to provide three (3) separate plungers for implantation of each of the three stents separately. FIG. 21 provides an example of a finger actuator that may be used to deliver a single stent. It can also be adapted to deliver two (2) or three (3) stents.

In FIG. 21, delivery apparatus 440 comprises a cannula 448 carrying stent 444 at one end thereof. A handle 450 is provided at the opposite end of cannula 448. A linger actuator 442 is also provided which is attached to plunger body 446 and plunger end 452. The finger actuator 442 can be advanced along a slot in the cannula in the direction of the arrow for exerting a force on the end of stent 444, which can be used to push stent 444 into the eye for implantation in a targeted space. Stent 444 has a sharpened tip which can facilitate formation of a hole its the tissue of the eye. Although not drawn to scale, it may be appreciated that the cannula has sufficient length to extend from the outside of the cornea of an eye to the targeted location with the handle and finger actuator also outside of the eye where they can be manipulated by a surgeon.

Figure 10:
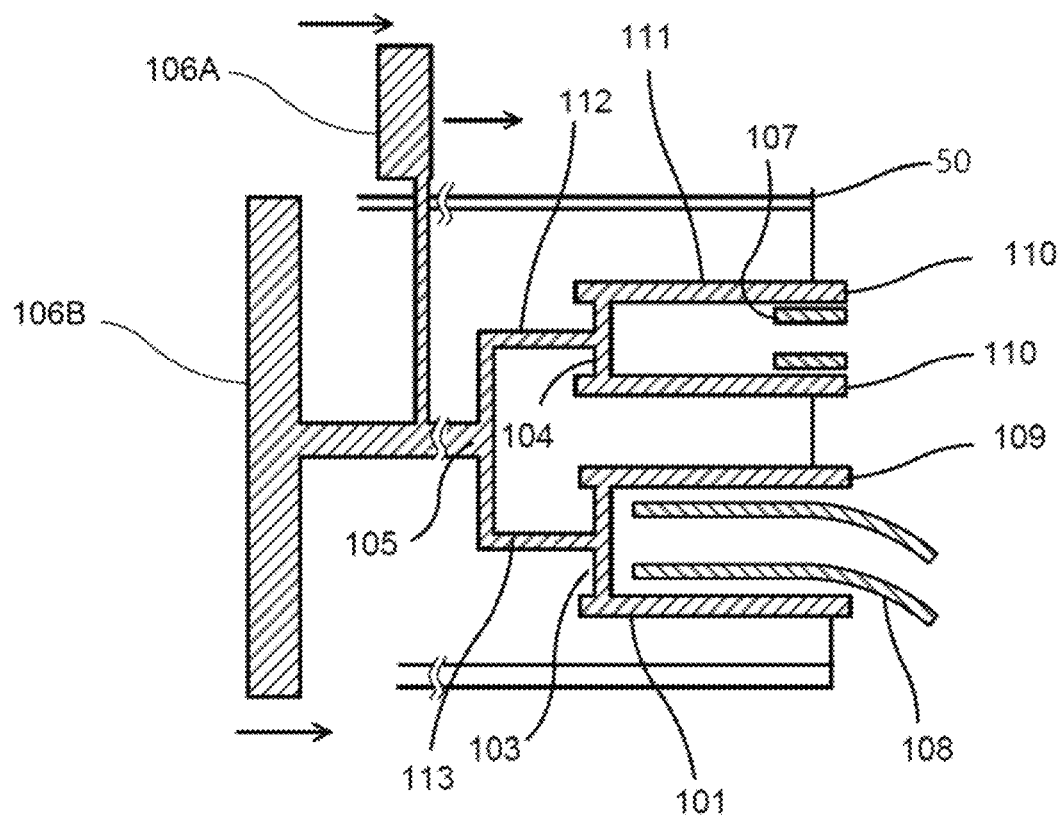
FIG. 10 is a schematic view of an exemplary inserter or actuator for causing a plurality of stents to be simultaneously pushed from a cannula and into an eye.

Referring now to FIG. 10, there is seen a preferred mechanism 100 for implanting stents simultaneously in another embodiment of the invention. FIG. 10 shows a bi-flow embodiment for implantation of two (2) stents, a soft stent 107 for implantation, for example, in the trabecular meshwork/Schlemm's canal and a rigid stent 108 for implantation, for example, in the suprachoroidal space. Stent 107 is carried in tubular channel 111 of cannula 50 whereas stent 108 is carried in tubular channel 109 of cannula 50. Since stent 108 is rigid, like those commercially available as the iStent® or CyPass®, the stent itself can be provided with puncturing means (e.g., a needle-like or blunt tip) for forming a hole in tissue of the eye through which the stent can be pushed. With a soft stent, such as stent 107, tubular channel 111 can be in the form of a needle with sharpened tip 110 for forming a hole in tissue through which the stent can then be pushed for implantation.

FIG. 10 shows alternative mechanisms by which stents 107 and 108 can be advanced out of their respective channels and into respective anatomical spaces in the eye. In a first mechanism, after cannula 50 is inserted into the eye with an end in the anterior chamber adjacent the trabecular meshwork, a force can be exerted against plunger 106B, crosspiece 105, prongs 112 and 113 and end pieces 103 and 104 to push stents 107 and 108 out of their respective channels. In a second mechanism, a slide piece 106A connected to crosspiece 10, prongs 112 and 113 can be provided for sliding through a slot in the cannula (not shown) to push the stents out of their respective channels. Although FIG. 10 is not drawn to scale, it may be readily appreciated that the cannula 50 and the respective plunger mechanisms can be dimensioned for ab interno implantation into the eye of a patient. Thus, a first end of the cannula carrying stents 107 and 108 can be inserted into the anterior chamber through an incision in the cornea that is remote from the implantation site such that the stents are disposed adjacent the trabecular meshwork with the plungers 106A and 106B projecting outside of the site of the corneal incision. With that disposition, either plunger 106B or slide piece 106A can be actuated by the hand of an operator (surgeon) from outside of the eye to push the stents out of their respective channels.

Still referring to FIG. 10, the individual plungers can be disposed at different distances from the stents for use with stents of different lengths. Thus, a shorter stent 107 (e.g., a stent targeted for the trabecular meshwork/Schlemm's canal) could be delivered after a longer stent 108 (e.g., a stent targeted for the suprachoroidal space) is already advanced to penetrate a target tissue. The shorter stent 107 could be placed in its channel but not delivered until the individual plunger 103 delivers the longer stent 108 first. For example, in a tri-flow embodiment, if a slide mechanism delivers a XEN® stent, CyPass® stent, and an iStent® stent and the XEN® stent is longer than the CyPass® stent, which is longer than the iStent®, the XEN® could be delivered first, the CyPass® next, and the iStent® last. While only two stents are shown in FIG. 10, it will be appreciated that three stents (i.e., the tri-flow embodiment) can be advanced using a similar slide mechanism.

Figure 15A:
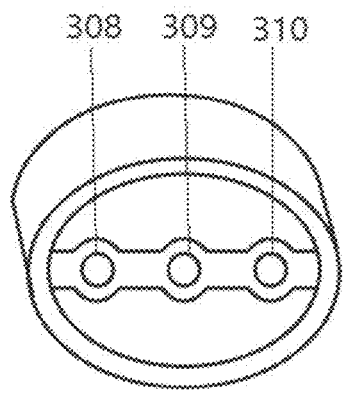
FIGS. 15A-E illustrate exemplary delivery vehicles for simultaneous implantation of three (3) stents into separate areas of a single anatomical space according to one embodiment of the invention.
Figure 15B:
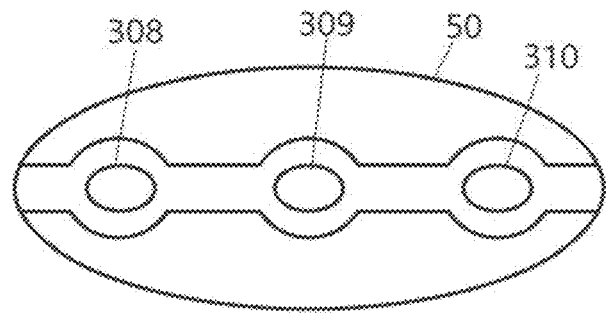
Figure 15D:
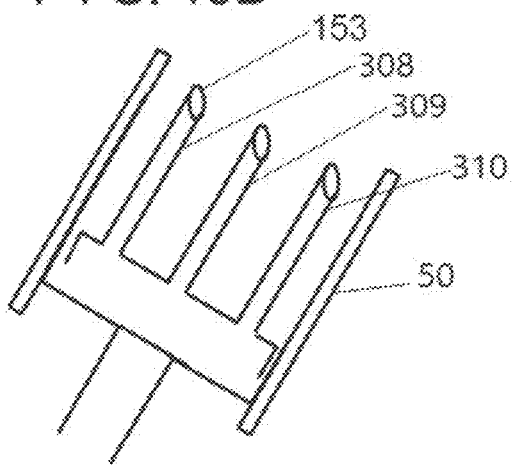
Figure 15C:
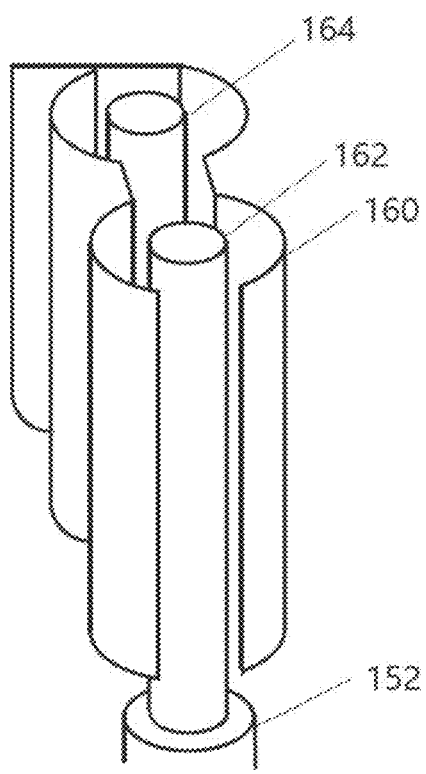
Figure 15E:
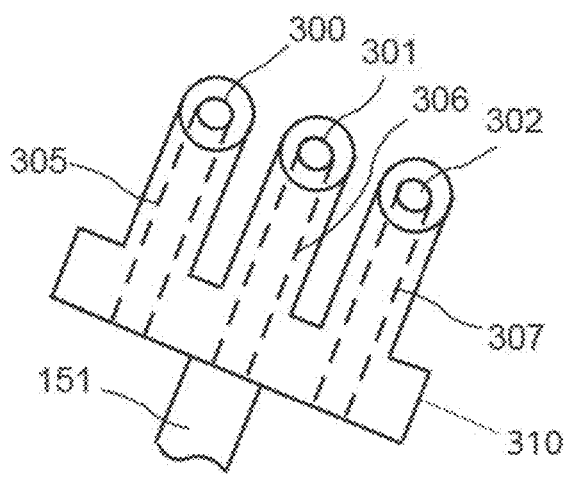

Referring to FIGS. 15A-E, there can be seen other exemplary delivery vehicles of the invention. FIGS. 15 A and B each depicts three (3) stents 308, 309, and 310 with sharpened tips disposed in cannula 50 for delivery of the stents into different areas of a single anatomical space, i.e., different areas of the subconjunctival space, Schlemm's canal or the suprachoroidal space. FIG. 15F comprises three stents 300, 301, and 302 carried in respective channels 305, 306, 307 of a delivery vehicle 310 and a plunger 151 for simultaneously pushing the three stents out of their respective channels until their outflow ends are all disposed in a single one of the preferred anatomical spaces, e.g., in the subconjunctival space, in the suprachoroidal space or in Schlemm's canal. As shown in FIG. 15E, the stents may preferably be provided with sharpened tips 153 for forming holes in eye tissue through which the stents can pass, although this is not necessary in this or the other embodiments since stents with blunt ends can also be used to form holes in the tissue of the trabecular meshwork. Unlike the other embodiments described above, in this embodiment of the invention, plunger 151 places the stents simultaneously in one of the outflow pathways, i.e., the trabecular meshwork/Schlemm's canal, or suprachoroidal space, or the subconjunctival space. In contrast, FIG. 15C shows stents 162 and 164 disposed in channel guide 160 wherein a separate plunger 152 is provided for pushing stent 162 out of the channel guide. Another plunger (not shown) can be provided for separate insertion of stent 164.

Referring to FIG. 18, there is shown another preferred delivery vehicle of the invention, which is analogous to that shown in FIGS. 15A-F. Actuator or hand piece 181 is shown disposed in the cannula for applying a force to the proximal ends 182A, 183A and 184A of the stents to cause them to be released from the cannula and implanted in the eye of a patient. Actuator 181 is depicted in the figure as having a base 181D with three (3) prongs 181A, 181B, and 181C. The prongs have ends which are respectively configured and dimensioned to fit within the channels 185, 186, and 187 and to contact the proximal ends 182A, 183A, and 184A of the stents to apply a suitable force thereto to cause simultaneous release and implantation of the stents when a corresponding force is applied to move the base 181D, either manually or by mechanical means.

Figure 22:
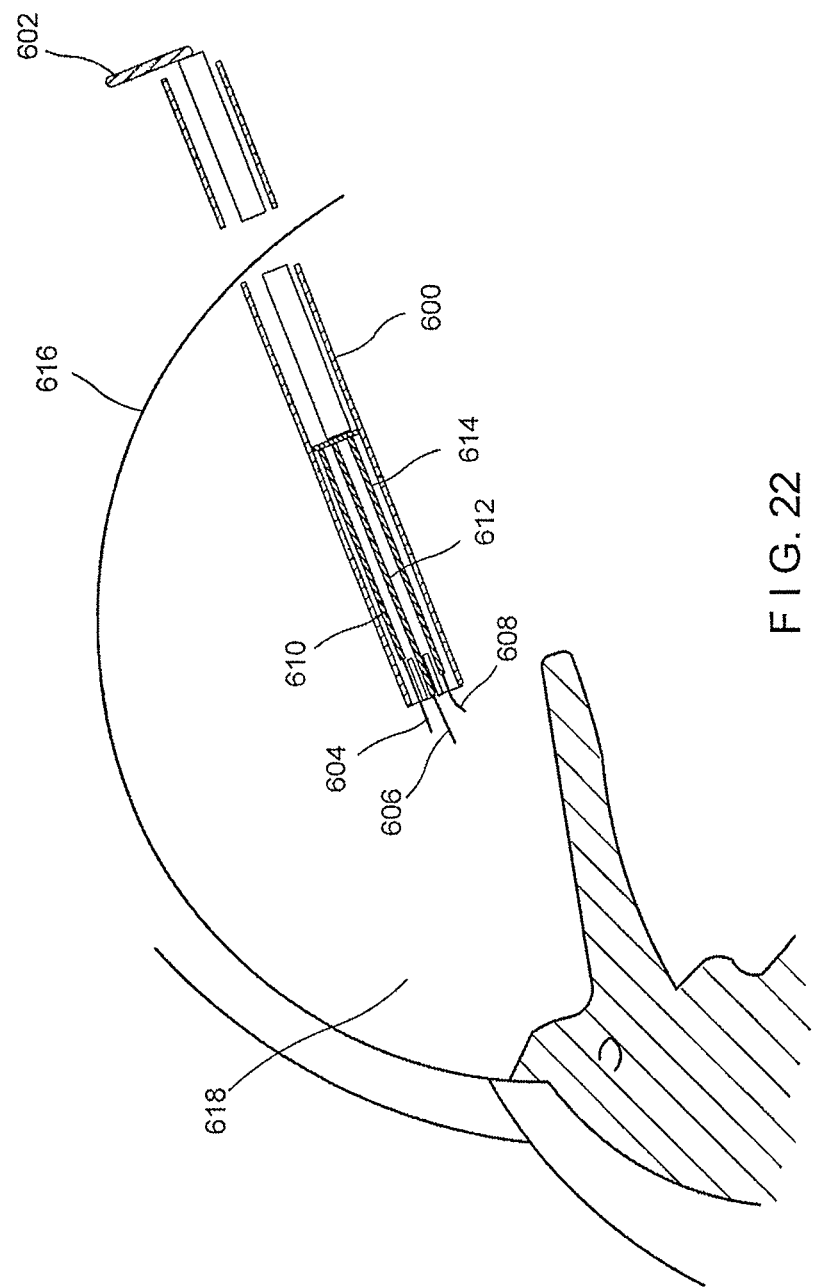
FIG. 22 shows the disposition of a cannula carrying a stent or plurality of stents into the anterior chamber with actuator disposed outside of the eye for ab inferno implantation of the stents.

FIG. 22 depicts the disposition of the delivery means, cannula 600 with channels 610, 612 and 614 carrying a plurality of stents 604, 606 and 608 in the tri-flow embodiment when the plurality of stents are being installed ab interno. The entry site of the delivery means carrying the stents is made through an incision at a location 616 remote from the site 618 adjacent to the trabecular meshwork at which the delivery means delivers the stents. Once a tip of the cannula is apposite the trabecular meshwork, the operator (surgeon) pushes or otherwise activates the actuator to push the stents through the trabecular meshwork and, in the case of the subconjunctival stent, through the sclera, and into the respective outflow channels where they are secured by friction. FIG. 16 is a schematic diagram showing the outflow ends of the respective subconjunctival, canal and suprachoroidal stents 141, 142 and 143 when implanted in the eye.

Reference is now made to FIGS. 7A-G, which show another embodiment of the invention in which a multi-sided deck or platform 70 has an array of shunts 71 integrated therein. The deck has first side 73 and second side 72. The array of shunts project from the second side 72 of the deck or platform only and are disposed to secure the deck to an inside surface of the trabecular meshwork by friction with the second side of the deck contacting the trabecular meshwork and the stunts in the array projecting through the trabecular mesh to the subconjunctival space, Schlemm's canal and/or the suprachoroidal space. See FIG. 6. The multiple shunts are preferably integral to the deck and are "stuck" into the trabecular meshwork and other structures of the eye in a manner that is analogous to the manner in which "tackless" wooden corner pieces are used to secure wall-to-wall carpeting. The shunts 71 projecting from the second side 72 are in fluid communication with the openings 74 in the first side 73 of the deck such that, with the deck secured to the trabecular meshwork and the stunts projecting through the trabecular meshwork to the subconjunctival space, Schlemm's canal and/or the suprachoroidal space, fluid can be drained from the anterior chamber to an anatomical space or spaces of lower pressure. The lumen size of the shunts 71 can be constant or variable, e.g., tapered to a point 75 so as to readily penetrate target tissues. Some or all of the shunts 71 can be temporarily occluded. The multiplicity of the shunts 71 and points would hold the device shown in FIGS. 7A-G securely in the eye.

For optimal stabilization of the device in the eye, the shunts are preferably disposed with respect to the deck at an acute and/or obtuse angle and are preferably tapered and of generally conical shape, although other shapes and orientations would work so long as they can perform the function of securing or stabilizing the device in the eye. Thus, the deck 70 may be of rectangular, circular or other shape, and the stents may be arranged on the second side of the deck in a plurality of rows or circumferentially so long as there are sufficient stents to secure the deck in the eye, preferably at least four (4), more preferably at least six (6), and most preferably at least eight (8). Preferred arrangements of the stunts 71 on deck 70 are shown in FIGS. 7A-G, FIG. 8 and FIG. 17. The distal ends of the projecting shunts 71 preferably have openings with a diameter of about 5 µm and proximal ends with openings of about 10 µm. The body of a rectangular deck will preferably be about 100 to 500 µm. The body of a circular deck will preferably be about 300 µm in diameter.

Figure 9:
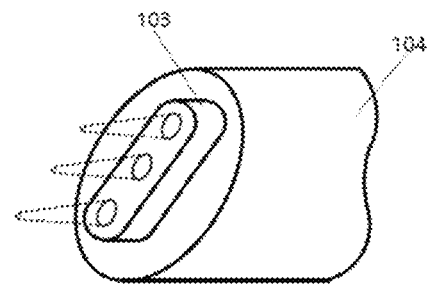
FIG. 9 illustrates a shunt tack disposed within a cannula for delivery into the eye.

Referring to FIGS. 8A-D, there are seen exemplary deck devices according to other embodiments of the invention. The deck 81 in the embodiment of FIG. 8A is a flat round disk with the tacks posterior. The deck 82 in the embodiment of FIG. 8B is a rounded disk with a depression 85 to thin the material with the tacks posterior (see FIG. 8C). The deck 83 in the embodiment of FIG. 8D is of rectangular shape. The cross-action forceps described below can be used for any of the shunt tack embodiments. Alternatively, a small plunger could be used centrally in the deck 82 of FIG. 8B to push the disk into position using a cannula. FIG. 9 shows a shunt tack 103 disposed with a friction fit in cannula 104 which can be used in this regard.

Figure 12:
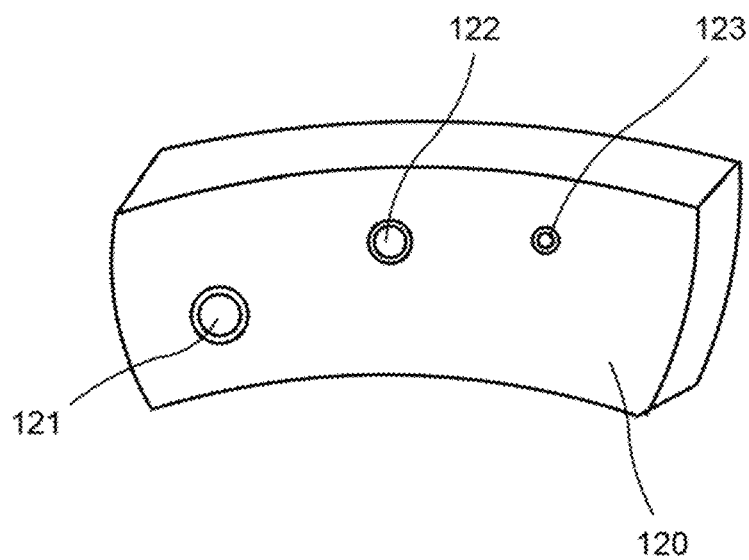
FIG. 12 illustrates an exemplary deck for tri-flow drainage of aqueous from the anterior chamber according to one embodiment of the present invention.

Referring now to FIG. 12, there is shown a further embodiment of the invention wherein a block 120 of biocompatible material in provided with three stents 121, 122, and 123 embedded therein and with ends of the stents projecting therefrom. Although a generally rectangular block is shown, the block can be of any shape, including oblong, round, ovoid or square. In FIG. 12, the small opening 123 can be disposed for targeting to the subconjunctival space (in the manner of, e.g., XEN®), the middle opening 122 can be disposed for targeting to the trabecular meshwork/Schlemm's canal (in the manner of, e.g., iStent®), and the largest opening 121 can be disposed for targeting to the suprachoroidal space (in the manner of, e.g., CyPass®). The individual stents 121, 122, and 123 may be provided with pointed or blunt tips for entering target tissues. Block 120 can be implanted in the eye adjacent the trabecular meshwork with the stents projecting through the trabecular meshwork with the respective ends of the stents disposed in the respective target spaces. Block 120 can be delivered into the anterior chamber inside of a cannula that has indicia indicating anterior/posterior location or it can be delivered with a holding/locking forceps that would deliver it to the target location without the use of a cannula. The forceps can be released once the block 120 is secured in the eye.

Figure 20A:
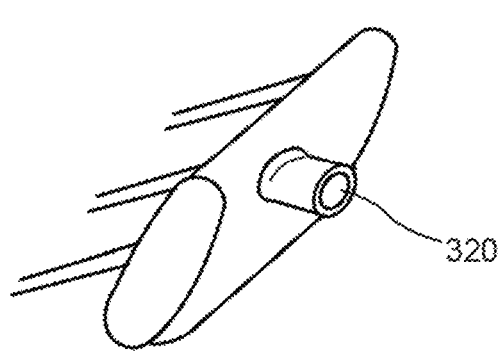
FIGS. 20A-C illustrate an exemplary shunt tack embodiment of the invention with a single inflow opening and a mechanism for delivery of the shunt tack into the anterior chamber.
Figure 20B:
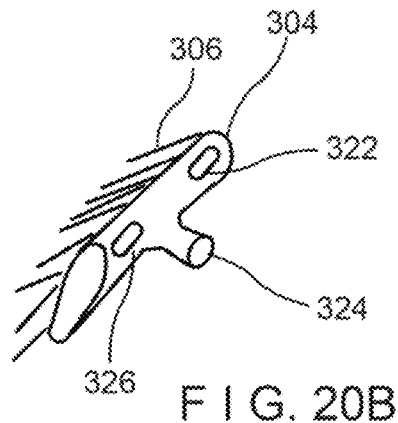
Figure 20C:
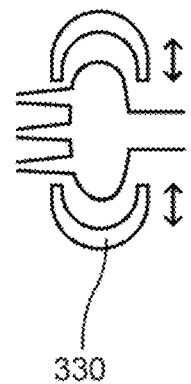

Referring to FIGS. 20A-C, there is shown an embodiment that is similar to that shown in FIG. 12, wherein a deck 304 is provided with stents 306 embedded therein with portions 306 projecting therefrom. The projecting portions 306 of the stents should be of sufficient length such that the outflow ends of the projecting portions are disposed in the targeted anatomical space or spaces for draining aqueous from the anterior chamber. Deck 304 can be provided with a single opening 320 for drainage of aqueous from the anterior chamber through the stents 306, as shown in FIG. 20A, or it can be provided with multiple openings 322, 324 and 326 for drainage of aqueous through the stents 306, as shown in FIG. 20B. FIG. 20C shows U shape ends of cross action forceps 330 that may be used to grasp and deliver the deck for implantation into the eye.

FIG. 6 shows the disposition of the deck 80 and forceps when the device is being installed in the eye ab interno. In FIG. 6, the deck 80 is disposed in the trabecular meshwork. The entry site of the delivery means carrying the stents is made through an incision 61 at a location remote from the site 62 adjacent the trabecular meshwork at which the forceps delivers the device. Once the deck is secured with the shunts projecting through the trabecular mesh and into the subconjunctival space, Schlemm's canal and/or suprachoroidal space, the forceps is released and removed from the eye. Reference numerals 84 and 86 show shunt tacks that have already be implanted. A shunt tack can also be placed in a cannula using forceps. If the shunt tack is made in a round or ovoid shape, then using a cannula might be more convenient, but a square or ovoid needle/cannula can also accommodate a rectilinear shunt tack.

Figure 19:
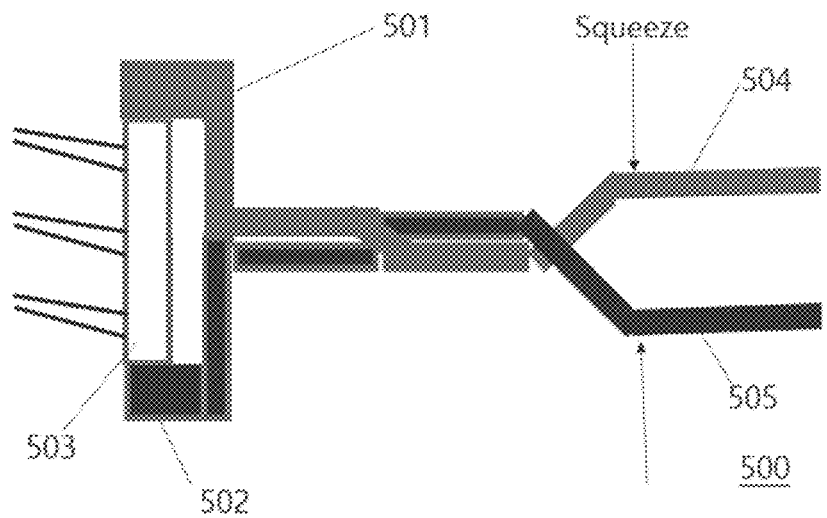
FIG. 19 shows forceps for use with a tack shunt embodiment of the invention.

FIG. 17 shows an implantable deck or body 176 with projecting stents releasably fit within a holding or delivery means, which in the figure comprise forceps 172 having a pair of pincers or tongs for securing the deck until it is positioned in the anterior chamber with the shunts or stents introduced into their appropriate outflow channel(s). The forceps can be used to insert the deck through an incision in the cornea that is remote from the site in which the deck is implanted into an eye. FIG. 17 shows reverse action forceps 172, which can hold the shunt tack device 176 until opposing ends 174 and 176 of the forceps are squeezed thereby releasing pincers 178 and 180 from the device once the device is implanted. FIG. 17 is not drawn to scale but it may be appreciated that, for ab interno insertion, the distance from screw hinge 181 to holding part 183 of the forceps should be longer than an inside of the corneal diameter of 13 mm, e.g. about 15 mm, and the hinge should be outside of the eye with the squeeze portion of the forceps preferably about 3-4" long. FIG. 19 shows exemplary cross action forceps 500 that can be used to deliver and implant the deck in another embodiment. Forceps 500 has a first end with pincers 501 and 502 that can be used to clamp on the body of a tack shunt 503 and a cross action mechanism that can move the pincers from a clamped position to a release position when ends 504 and 505 of the forceps are squeezed. The ends 504 and 505 of the forceps can be squeezed from outside of the eye to release the forceps from the clamped position and the forceps can then be withdrawn through the remote incision in the cornea with the tack shunt implanted in the eye.

Each of the embodiments of the invention may comprise means for preferential occlusion of drainage into one of the anatomical spaces, preferably the subconjunctival space, on a temporary basis. Inflammation is believed to be the issue in failure for most glaucoma surgeries that dram into the subconjunctival space (Trabeculectomy, Tube Shunt Drainage Devices, XEN). These drainage sites have been demonstrated to have pro inflammatory molecules called cytokines coming from the aqueous in the anterior chamber. It has been shown that, by reducing the flow of cytokines into the subconjunctival space by closing off the aqueous drainage for a period of time, the procedures are more successful. A preferred way of doing this is temporarily to close off the shunts or openings by occluding them. A problem with this is IOP increases post operatively and, when the occlusion stops, very low IOP can cause bleeding into the eye. With the use of shunts of the invention having multiple outflow pathways, this problem can be alleviated by preferentially closing off one or more of the pathways, e.g., a pathway or pathways to the subconjunctival space, without closing off other of the pathways whereby to allow drainage through the other pathways.

Figure 11:
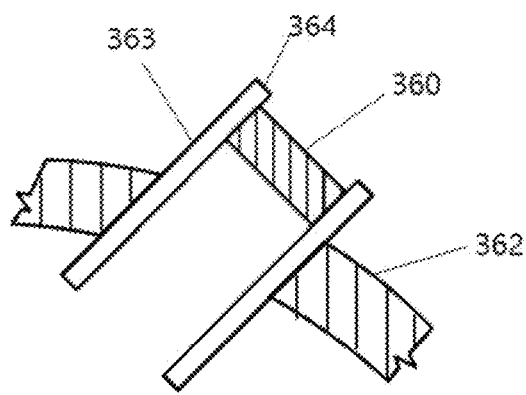
FIG. 11 illustrates an exemplary subconjunctival shunt with means for occlusion of the outflow pathway of the shunt.

Means for temporary occlusion of individual pathways are well known in the art and include, by way of example: sponges with occlusion from biodegradable coatings, biodegradable polymers with anti-inflammatory/anti-infections properties and sponges acting as shunts in the subconjunctival space. The use of sponges with biodegradable coatings and biodegradable polymers with anti-inflammatory/anti-infectious properties are described, for example, in U.S. Pat. No. 7,655,831 to Prywes and U.S. Pat. No. 5,346,464 to Camras, which are incorporated herein by reference. The use of a sponge as a stent which occludes flow of aqueous from the anterior chamber to the subconjunctival space is described in the inventor's U.S. Pat. No. 7,655,831, the entire contents of which are incorporated herein by reference. The sponge is constructed and arranged to occlude flow of aqueous from the anterior chamber to the subconjunctival space until a pressure in the anterior chamber increases to force the fluid through the sponge into the subconjunctival space. FIG. 11 shows a stent 363 engaged with membrane 362 having a sponge 360 occluding an end 364 of the stent. In another preferred aspect of the first embodiment of the present invention, a sponge can be used as the stent that is implanted for drainage of aqueous from the anterior chamber into the subconjunctival space.

A preferred method of installation of the shunt valves or stents of the invention is that the valves are engaged with the trabecular meshwork and/or sclera in the direction from within the anterior chamber to the subconjunctival space, the entry site of the valves and delivery tool being made at a location remote from the site at which the valve is implanted in the sclera. Specifically, a small incision is made in the cornea to permit insertion of the valves and the delivery tool into the interior of the anterior chamber. Installation of the valve into the respective membrane or wall therefore, takes place from within the eye. Prior to insertion of the valves and a delivery instrument into the anterior chamber, a viscoelastic fluid is injected into the anterior chamber to prevent collapse of the anterior chamber. A saline solution may be injected into the anatomical space to inflate the space and form a "bleb." The delivery instrument with the valves externally mounted on its end is then inserted, valve-first, through the incision in the cornea. The instrument may be inserted substantially parallel to the iris to avoid contact with the corneal endothelium. When the instrument is located in a position adjacent the trabecular meshwork, the operator (surgeon) activates the cutting means, by for example pushing a cannula having respective channels with sharpened tips, to form respective holes in a membrane or membranes through which the respective valves may then be advanced through the respective holes to position their ends in the respective anatomical spaces. The lumens of the membrane or membranes though which the valves are advanced have sufficient flexibility to allow the valves to penetrate into the holes and, when the valve has been advanced a sufficient distance, the membrane(s) will elastically engage the valves so that they are elastically retained. When the valves have been implanted, the delivery instrument is withdrawn and removed through the incision in the cornea.

After the valves have been implanted and the instrument has been removed a suture may (optionally) be placed to close the incision. Since the incision is distant from the implant site, there is minimum trauma to the eye at the implant site.

Although the invention has been described with reference to the preferred method of installation of the shunt valve in the direction from the anterior chamber to the subconjunctival space, it is also possible to implant the valve in the sclera working from outside the eye through the subconjunctival space into the anterior chamber. In this variation of the invention, an initial incision is made in the eye at a location distant from the implant site of the valve, and the delivery instrument with the valves thereon is introduced through the incision to bring the end of the tool into proximity with the membranes at the location where the hole is to be formed. The valves will then be disposed on or in the instrument in a reversed position from how they are disposed for insertion ab interno. As in the ab interno embodiment, the instrument forms the hole in the sclera where after the valves are inserted into the formed holes and engage with the respective membranes. After the valves have been implanted, the delivery instrument is withdrawn.

The method of installation according to the ab inferno approach is preferred insofar as the valves may be implanted and retained in place without any sutures and with the formation only of a small incision distant from the implant sites. The valves are inserted with the same instrument that forms the bole in the elastic membranes. The valves can be made as one piece and installed in a single step surgical operation or it can be a two-piece unit with a subsequently added module in a two-step operation.

While the invention has been described with reference to preferred embodiments thereof it will be apparent to those skilled in the art that numerous modifications and variations can be made within the scope and spirit of the invention as defined in the attached claims.

What is claimed is:

1. An apparatus for relieving intraocular pressure in an eye of a subject, the apparatus comprising:

(a) a plurality of stents, including at least (i) a first stent sized and configured for being implanted in the eye through a hole in a first membrane separating a high pressure chamber of the eye from a first anatomical space of lower pressure than the high pressure chamber in a first disposition with an inlet end of the first stent in the high pressure chamber and an outlet end of the first stent in the first anatomical space to permit drainage of fluid from the high pressure chamber to the first anatomical space and with a portion of the first stent engaging with the first membrane to stabilize and retain the first stent in the first disposition, and (ii) a second stent sized and configured for being implanted in the eye through a hole in a second membrane separating the high pressure chamber of the eye front a second anatomical space of lower pressure than the high pressure chamber in a second disposition with an inlet end of the second stent in the high pressure chamber and an outlet end of the second stent in the second anatomical space to permit drainage of fluid from the high pressure chamber to the second anatomical space and with a portion of the second stent engaging with the second membrane to stabilize and retain the second stent in the second disposition; wherein the high pressure chamber is the anterior chamber of the eye, wherein each of the first and second anatomical spaces is selected from the group consisting of a subconjunctival space, Schlemm's canal and a suprachoroidal space, and wherein the first anatomical space and the second anatomical space can be different areas of same anatomical space;

(b) delivery means for releasably carrying at least the first stent and the second stent together through a single incision in the cornea of the eye to a first position in the anterior chamber of the eye that is adjacent the trabecular meshwork and for holding the first and second stents at said position in an anterior to posterior configuration until the first and second stents are released from the delivery means, the delivery means comprising means for forming respective holes in the first and second membranes through which the first and second stents are insertable or each of the first and second stents comprising an end that can form respective holes in the first and second membranes through which the first and second stents are respectively insertable; the first and second stents being disposed in the delivery means and being respectively sized and configured such that, with the delivery means in the first position and with application of a force to each of the first and second stents, each of the first and second stents is releasable from the delivery means and implantable into the eye through the respective holes formed in the first and second membranes and into the first and second dispositions respectively; and (c) actuating means for applying a force to each of the first and second stents to cause the first and second stents to be simultaneously released from the delivery means and implanted into the eye with the first and second stents in the first and second dispositions respectively.

2. The apparatus according to claim 1, wherein the apparatus comprises means for temporarily occluding drainage of fluid passing through the first stent from the anterior chamber into the subconjunctival space with the first stent implanted into the eye in the first disposition without occluding drainage of fluid through the second stent.

3. The apparatus according to claim 1, wherein the delivery means comprises a cannula having an anterior surface and a posterior surface and at least first and second channels for retaining the first and second stents respectively with a friction fit, wherein the cannula comprises means for differentiating the anterior and posterior surfaces, and wherein the first stent and the second stent are disposed within the cannula in an anterior to posterior orientation.

4. The apparatus according to claim 1, wherein the first stent is disposed in the delivery means and is sized and configured for implantation into the eye with the inflow end of the first stent in the anterior chamber and the outflow end of the first stent in the subconjunctival space and wherein the second stent is disposed in the delivery means and is sized and configured for implantation into the eye with the inflow end of the second stent in the anterior chamber and the outflow end of the second stent in Schlemm's canal.

5. The apparatus according to claim 1, wherein the first stent is disposed in the delivery means and is sized and configured for implantation into the eye with the inflow end of the first stent in the anterior chamber and the outflow end of the first stent in, the subconjunctival space and wherein the second stent is disposed in the delivery means and is sized and configured for implantation into the eye with the inflow end of the second stent in the anterior chamber and the outflow end of the second stent in the suprachoroidal space.

6. The apparatus according to claim 1, wherein the first stent is disposed in the delivery means and is sized and configured for implantation into the eye with the inflow end of the first stent in the anterior chamber and the outflow end of the first stent in the Schlemm's canal and wherein the second stent is disposed in the delivery means and is sized and configured for implantation into the eye with the inflow end of the second stent in the anterior chamber and the outflow end of the second stent in the suprachoroidal space.

7. The apparatus according to claim 1, wherein the first anatomical space and the second anatomical space are different areas of the subconjunctival space.

8. The apparatus according to claim 1, wherein the plurality of stents further comprises a third stent, the third stent being sized and configured for being implanted in the eye through a hole in a third membrane separating the anterior chamber of the eye from a third anatomical space of lower pressure than the anterior chamber in a third disposition with an inlet end of the third stent in the anterior chamber and an outlet end of the third stent in the third anatomical space to permit drainage of fluid from the anterior chamber to the third anatomical space and with a portion of the third stent engaging with a third membrane to stabilize and retain the third stent in the third disposition, the hole forming means comprising means for forming a hole in the third membrane through which the third stent is insertable or the third stent comprising an end for forming a hole in the third membrane through which the third stent is insertable; the first, second and third stents being disposed in the delivery means and being sized and configured such that, when the delivery means is in the first position adjacent to the trabecular meshwork and an actuation force is applied to each of the first, second and third stents, the first, second and third stents are implantable into the eye in the first, second and third dispositions respectively with the inflow end of the first stent in the anterior chamber and the outflow end of the first stent in the subconjunctival space, with the inflow end of the second stent in the anterior chamber and the outflow end of the second stent in Schlemm's canal and with an inflow end of the third stent in the anterior chamber and an outflow end of the third stent in the suprachoroidal space.

9. The apparatus according to claim 8, wherein the apparatus comprises means for temporarily occluding drainage of fluid passing through the first stent from the anterior chamber into the subconjunctival space with the first stent implanted into the eye in the first disposition without occluding drainage of fluid passing through the second or third stent from the anterior chamber into Schlemm's canal and the suprachoroidal space with the second and third stents implanted into the eye in the second and third dispositions respectively.

10. The apparatus according to claim 9, wherein the delivery means comprises a cannula having an anterior surface and a posterior surface and first, second and third channels for retaining the first, second and third stents respectively, wherein the cannula comprises means for differentiating the anterior and posterior surfaces, and wherein the first stent and the second stent are disposed within the cannula closer to the anterior surface than the third stent.

11. The apparatus according to claim 10, wherein the actuating means comprises a first mechanism comprising a first end with a first slidable member that is slidable relative to the cannula when pushed by a hand of a user, the first mechanism having a second end with means for simultaneously pushing the second stent and third stents out of the second and third channels and implanting them into the eye in the second and third dispositions respectively when the first slidable member is slid along the first surface toward the second and third stents, and wherein the actuating means further comprises a second mechanism comprising a first end with a second slidable member that is slidable relative to the cannula when pushed by a hand of a user, the second mechanism having a second end with means for pushing the first stent out of the first channel and implanting it into the eye in the first disposition when the second slidable member is slid toward the second and third stent and into the eye in the first disposition.

12. A method for relieving intraocular pressure in an eye of a subject comprising the steps of:
 (a) providing the apparatus of claim 1;
 (b) inserting a first end of the delivery means carrying the first stent and the second stent together through a single incision in the cornea of the eye to a position in the anterior chamber of the eye that is adjacent the trabecular meshwork; and
 (c) actuating the actuating means from a position at a second end of the delivery means that is outside of the eye to force to each of the first and second stents to cause the first and second stents to be simultaneously released from the delivery means and implanted into the eye with the first and second stents in the first and second dispositions respectively.

* * * * *